(12) United States Patent
Calderoni (10) Patent No.: US 11,005,291 B2
(45) Date of Patent: *May 11, 2021

(54) NON-CONTACT SURGICAL ADAPTER ELECTRICAL INTERFACE

(71) Applicant: Covidien LP, Mansfield, MA (US)

(72) Inventor: Anthony Calderoni, Bristol, CT (US)

(73) Assignee: Covidien LP, Mansfield, MA (US)

( * ) Notice: Subject to any disclaimer, the term of this patent is extended or adjusted under 35 U.S.C. 154(b) by 224 days.

This patent is subject to a terminal disclaimer.

(21) Appl. No.: 16/227,552

(22) Filed: Dec. 20, 2018

(65) Prior Publication Data

US 2019/0123583 A1    Apr. 25, 2019

Related U.S. Application Data

(63) Continuation of application No. 14/522,873, filed on Oct. 24, 2014, now Pat. No. 10,164,466.
(Continued)

(51) Int. Cl.
*A61B 17/00* (2006.01)
*H02J 50/10* (2016.01)
(Continued)

(52) U.S. Cl.
CPC .............. *H02J 50/10* (2016.02); *A61B 17/00* (2013.01); *A61B 17/07207* (2013.01);
(Continued)

(58) Field of Classification Search
CPC .. H02J 50/10; H02J 5/005; H02J 7/025; H02J 50/80; H04B 5/0081; H04B 5/0037;
(Continued)

(56) References Cited

U.S. PATENT DOCUMENTS 2,777,340 A    1/1957 Hettwer et al.
2,957,353 A    10/1960 Babacz
(Continued)

FOREIGN PATENT DOCUMENTS

AU    2008229795 A1    4/2009
CA    2451558 A1    1/2003
(Continued)

OTHER PUBLICATIONS

Chinese Office Action dated Mar. 4, 2019 issued in Chinese Application No. 2014108417658.
(Continued)

*Primary Examiner* — Daniel J Cavallari
(74) *Attorney, Agent, or Firm* — Carter, DeLuca & Farrell LLP (57) ABSTRACT

A surgical instrument includes a handle, an adaptor, and a non-contact electrical interface. A proximal end of the adaptor is releasably coupled to a distal end of the handle. The non-contact electrical interface is configured to wirelessly transmit energy from the handle to the adaptor and is configured to wirelessly transmit data from the adaptor to the handle. The electrical interface may include a proximal coil disposed within the handle and a distal coil disposed within the adaptor. When the adaptor is coupled to the handle, the proximal coil may be disposed adjacent the distal coil to form a transformer to inductively transfer energy from the handle to the adaptor and inductively transmit data from the adaptor to the handle.

16 Claims, 6 Drawing Sheets

Related U.S. Application Data (60) Provisional application No. 61/980,724, filed on Apr. 17, 2014.

(51) Int. Cl.
  H02J 7/02 (2016.01)
  H04B 5/00 (2006.01)
  A61B 17/072 (2006.01)
  A61B 90/98 (2016.01)
  H02J 5/00 (2016.01)
  *A61B 90/00* (2016.01)
  *H02J 50/80* (2016.01)

(52) U.S. Cl.
  CPC .............. *A61B 90/98* (2016.02); *H02J 5/005* (2013.01); *H02J 7/025* (2013.01); *H04B 5/0037* (2013.01); *H04B 5/0081* (2013.01); *A61B 2017/00022* (2013.01); *A61B 2017/0046* (2013.01); *A61B 2017/00075* (2013.01); *A61B 2017/00084* (2013.01); *A61B 2017/00199* (2013.01); *A61B 2017/00221* (2013.01); *A61B 2017/00398* (2013.01); *A61B 2017/00411* (2013.01); *A61B 2017/00473* (2013.01); *A61B 2017/00477* (2013.01); *A61B 2017/00734* (2013.01); *A61B 2090/0811* (2016.02); *H02J 50/80* (2016.02)

(58) Field of Classification Search
  CPC ... A61B 90/98; A61B 17/07207; A61B 17/00; A61B 2017/00075; A61B 2017/00084; A61B 2090/0811; A61B 2017/00398; A61B 2017/00473; A61B 2017/00022; A61B 2017/00199; A61B 2017/00411; A61B 2017/00221; A61B 2017/0046; A61B 2017/00477; A61B 2017/00734
  See application file for complete search history.

(56) References Cited

U.S. PATENT DOCUMENTS

| | | | |
|---|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,326,884 B1 | 12/2001 | Wohlrabe |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |

(56) References Cited

U.S. PATENT DOCUMENTS

| | | |
|---|---|---|
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,443,476 B2 | 5/2013 | Hilscher et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |

(56) References Cited

U.S. PATENT DOCUMENTS

| | | |
|---|---|---|
| 2006/0259073 A1 | 11/2006 | Miyamoto et al. |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0055219 A1 | 3/2007 | Whitman et al. |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167671 A1 | 7/2008 | Giordano et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209990 A1 | 8/2009 | Yates et al. |
| 2009/0254094 A1 | 10/2009 | Knapp et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2010/0268250 A1 | 10/2010 | Stuart et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0174861 A1* | 7/2011 | Shelton, IV ............ A61B 90/98 227/175.1 |
| 2011/0184245 A1 | 7/2011 | Xia et al. |
| 2011/0204119 A1 | 8/2011 | McCuen |
| 2011/0208170 A1 | 8/2011 | Hafner et al. |
| 2011/0218522 A1 | 9/2011 | Whitman |
| 2011/0251606 A1* | 10/2011 | Kerr .................. A61B 18/1402 606/34 |
| 2011/0253765 A1 | 10/2011 | Nicholas et al. |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0075443 A1 | 3/2013 | Giordano et al. |
| 2013/0093149 A1 | 4/2013 | Saur et al. |
| 2013/0098966 A1 | 4/2013 | Kostrzewski et al. |
| 2013/0098968 A1 | 4/2013 | Aranyi et al. |
| 2013/0098969 A1 | 4/2013 | Scirica et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0005681 A1 | 1/2014 | Gee et al. |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0144970 A1 | 5/2014 | Aranyi et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0373652 A1 | 12/2014 | Zergiebel et al. |
| 2015/0157321 A1 | 6/2015 | Zergiebel et al. |
| 2015/0164502 A1 | 6/2015 | Richard et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |

FOREIGN PATENT DOCUMENTS

| | | |
|---|---|---|
| CN | 102247182 A | 11/2011 |
| CN | 10340244 | 11/2013 |
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |

(56) References Cited

FOREIGN PATENT DOCUMENTS

| | | | |
|---|---|---|---|
| EP | 1813211 | A2 | 8/2007 |
| EP | 1943954 | A2 | 7/2008 |
| EP | 1943956 | A2 | 7/2008 |
| EP | 1943958 | A1 | 7/2008 |
| EP | 1943976 | A2 | 7/2008 |
| EP | 2005898 | A2 | 12/2008 |
| EP | 2027819 | A1 | 2/2009 |
| EP | 2044890 | A1 | 4/2009 |
| EP | 2055243 | A2 | 5/2009 |
| EP | 2098170 | A2 | 9/2009 |
| EP | 2100561 | A2 | 9/2009 |
| EP | 2100562 | A2 | 9/2009 |
| EP | 2165664 | A2 | 3/2010 |
| EP | 2236098 | A2 | 10/2010 |
| EP | 2263568 | A2 | 12/2010 |
| EP | 2272443 | A1 | 1/2011 |
| EP | 2316345 | A1 | 5/2011 |
| EP | 2324776 | A2 | 5/2011 |
| EP | 2329773 | A1 | 6/2011 |
| EP | 2333509 | A1 | 6/2011 |
| EP | 2462878 | A1 | 6/2012 |
| EP | 2462880 | A2 | 6/2012 |
| EP | 2491872 | A1 | 8/2012 |
| EP | 2586382 | A2 | 5/2013 |
| EP | 2606834 | A2 | 6/2013 |
| EP | 2668910 | A2 | 12/2013 |
| EP | 2676615 | A2 | 12/2013 |
| EP | 2684530 | A1 | 1/2014 |
| ES | 2333509 | A1 | 2/2010 |
| JP | 08038488 | | 2/1996 |
| JP | 2005125075 | A | 5/2005 |
| KR | 20120022521 | A | 3/2012 |
| WO | 9915086 | A1 | 4/1999 |
| WO | 0072760 | A1 | 12/2000 |
| WO | 0072765 | A1 | 12/2000 |
| WO | 03000138 | A2 | 1/2003 |
| WO | 03013372 | A2 | 2/2003 |
| WO | 03026511 | A1 | 4/2003 |
| WO | 03030743 | A2 | 4/2003 |
| WO | 03065916 | A1 | 8/2003 |
| WO | 03077769 | A1 | 9/2003 |
| WO | 03090630 | A2 | 11/2003 |
| WO | 2004107989 | A1 | 12/2004 |
| WO | 2006042210 | A2 | 4/2006 |
| WO | 2007016290 | A2 | 2/2007 |
| WO | 2007026354 | A1 | 3/2007 |
| WO | 2007137304 | A2 | 11/2007 |
| WO | 2008131362 | A2 | 10/2008 |
| WO | 2008133956 | A2 | 11/2008 |
| WO | 2009039506 | A1 | 3/2009 |
| WO | 2007014355 | A3 | 4/2009 |
| WO | 2009132359 | A2 | 10/2009 |
| WO | 2009143092 | A1 | 11/2009 |
| WO | 2009149234 | A1 | 12/2009 |
| WO | 2011108840 | A2 | 9/2011 |
| WO | 2012040984 | A1 | 4/2012 |
| WO | 2014134027 | A2 | 9/2014 |

OTHER PUBLICATIONS

Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
European Search Report dated Dec. 22, 2015, issued in European Application No. 14199783.
Partial European Search Report dated Sep. 3, 2015, issued in European Application No. 14199783.
Japanese Office Action dated Sep. 18, 2018 cited in Japanese Appln. No. 2014251764.

* cited by examiner

NON-CONTACT SURGICAL ADAPTER ELECTRICAL INTERFACE

CROSS-REFERENCE TO RELATED APPLICATIONS

This application is a continuation of U.S. patent application Ser. No. 14/522,873, filed Oct. 24, 2014, which claims the benefit of and priority to U.S. Provisional Patent Application Ser. No. 61/980,724, filed Apr. 17, 2014. The entire contents of each of the above applications are hereby incorporated by reference.

BACKGROUND

1. Technical Field

The present disclosure relates to surgical instruments and, more specifically, to non-contact electrical interfaces for surgical instruments.

2. Discussion of Related Art

Powered surgical instruments generally have a handle portion and a working portion extending from the handle portion that contacts a patient. The working portion may require energy to power elements thereof and may gather data from a plurality of sensors thereof. Power may be transferred from the handle portion to the working portion and data may be transferred from the working portion to the handle portion through an electrical interface. Traditionally the electrical interface includes galvanic electrical connections allowing the working portion to detach from the handle portion. After each use, the powered surgical instrument is disposed of, reused, or partially disposed of and partially reused. Any part of a powered surgical instrument that is reused must be sterilized, by autoclaving, to neutralize potentially infectious agents before being reused.

The autoclave process has been used for many years to sterilized reusable surgical instruments. However, galvanic electrical connections are susceptible to damage from the steam and the high-pressure used in the autoclave process. For example, during the autoclave process the galvanic electrical connections can corrode, form dendtric growths, or electro-plate.

Accordingly, a continuing need exists for electrical contacts that are not susceptible to the autoclave process that can pass electrical power and data signals between a working portion and a handle portion of a surgical instrument.

SUMMARY

In the following aspects of the present disclosure, a non-contact electrical interface may pass power from a handle portion to a working portion of a surgical instrument and simultaneously pass a data signal from the working portion to the handle portion and/or from the handle portion to the working portion.

In an aspect of the present disclosure, a surgical instrument includes a handle, an adaptor, and a non-contact electrical interface formed therebetween. The adaptor includes a proximal end that is releasably coupled to a distal end of the handle. The non-contact electrical interface is configured to wirelessly transfer energy from the handle to the adaptor and to wirelessly transmit data from the adaptor to the handle.

In aspects, the handle includes a protrusion and the adaptor defines a recess. The recess of the adaptor receives the protrusion of the handle when the adaptor is coupled to the handle. The electrical interface includes a proximal electrical coil that is disposed within the protrusion of handle and a distal electrical coil disposed within the adaptor at a location adjacent the recess. When the adaptor is coupled to the handle, the proximal and distal electrical coils may form a transformer. The proximal electrical coil may inductively transfer a constant supply of energy to the distal electrical coil. In embodiments, an energy source is disposed within the handle that is electrically coupled to the proximal electrical coil. In some embodiments, an energy storage device is disposed within the adapter that is electrically coupled to the distal electrical coil. The energy storage device may be configured to store energy from the energy source. In certain embodiments, the electrical interface includes a signal processor disposed within the adaptor. The energy storage device may be configured to energize the signal processor.

In some aspects, the electrical interface includes a signal processor disposed within the adaptor that is configured to transmit high frequency signals data signals to the distal electrical coil. The energy storage device may be configured to energize a plurality of sensors. Each of the plurality of sensors may provide data signals to the signal processor.

In certain aspects, the electrical interface includes a control circuit that is configured to wirelessly transmit control signals from the handle to the adaptor. The control circuit may include a proximal control coil that is disposed within the protrusion of the handle and a distal control coil disposed within the adaptor at a location adjacent to the recess. The proximal and distal control coils may form a control transformer when the adaptor is coupled to the handle. The control transformer may inductively transmit control signals from the handle to the adaptor. In embodiments, the handle includes a control interface and the electrical interface includes a processor disposed within the handle. The processor may be configured to receive control inputs from the control interface and to receive data from the adaptor. The processor may be configured to generate control signals from the control inputs and from the data. The processor may transmit the control signals to the proximal control coil.

In particular aspects, the surgical instrument includes a loading unit that is releasably coupled to a distal end of the adaptor. The loading unit and the adaptor form a second electrical interface. The second electrical interface is configured to inductively transfer energy from the adaptor to the loading unit and is configured to inductively transmit data signals from the loading unit to the adaptor.

In other aspects of the present disclosure, a method of communication between components of a surgical instrument includes providing a surgical instrument including a handle and an adaptor, coupling a proximal end of the adaptor to a distal end of the handle to form a non-contact electrical interface, using the non-contact electrical interface to wirelessly transfer energy from the handle to the adaptor, and using the non-contact electrical interface to wirelessly transmit data from the adaptor to the handle. The surgical instrument may be any of the surgical instruments disclosed herein.

In aspects, forming the non-contact electrical interface includes positioning a proximal coil disposed within the handle adjacent a distal coil disposed within the adaptor to form a transformer. Wirelessly transferring energy from the energy source may include inductively transferring energy across the transformer from the handle to the adaptor. Wirelessly transmitting data from the adaptor to the handle may include inductively transmitting data across the transformer from the adaptor to the handle.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, wherein.

DETAILED DESCRIPTION

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 1:
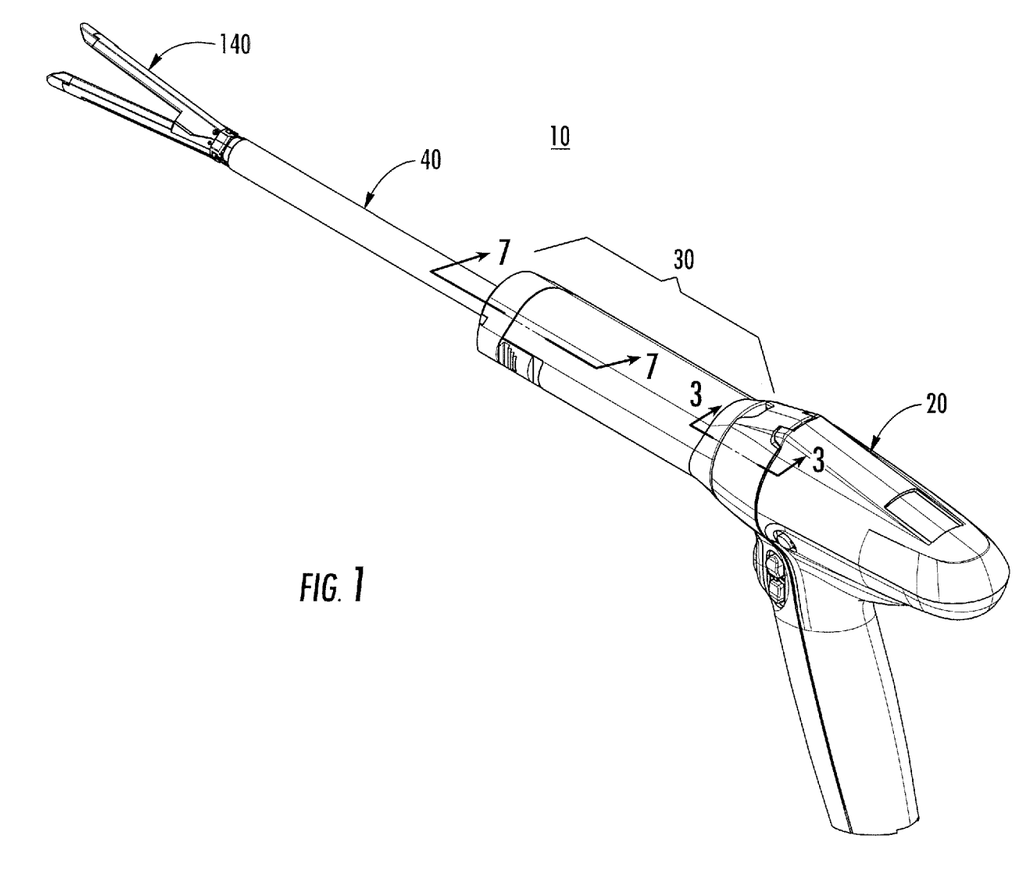
FIG. 1 is a perspective view of a surgical instrument provided in accordance with the present disclosure.
Figure 2:
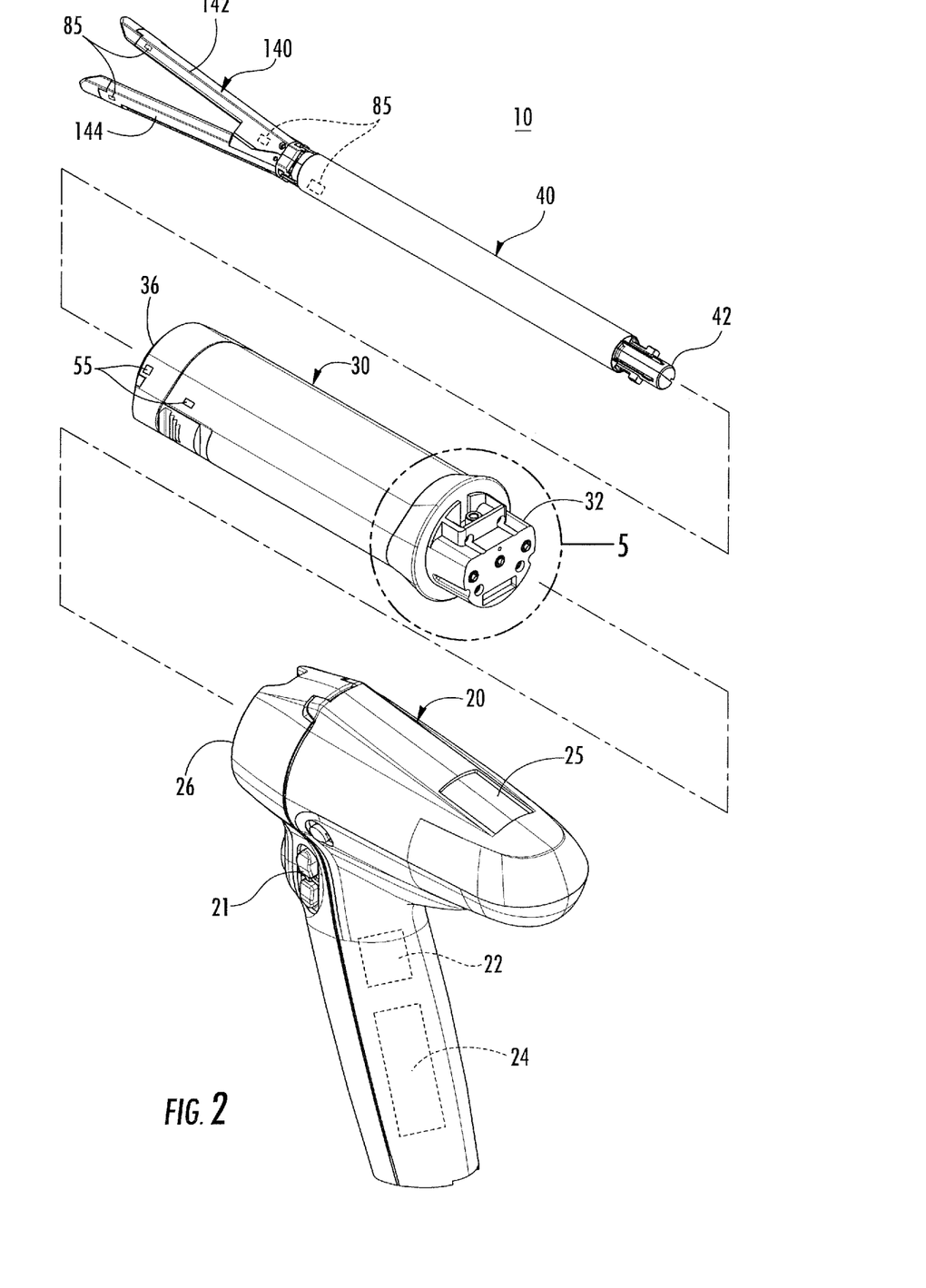
FIG. 2 is an exploded view of the components of the surgical instrument of FIG. 1.
Figure 3:
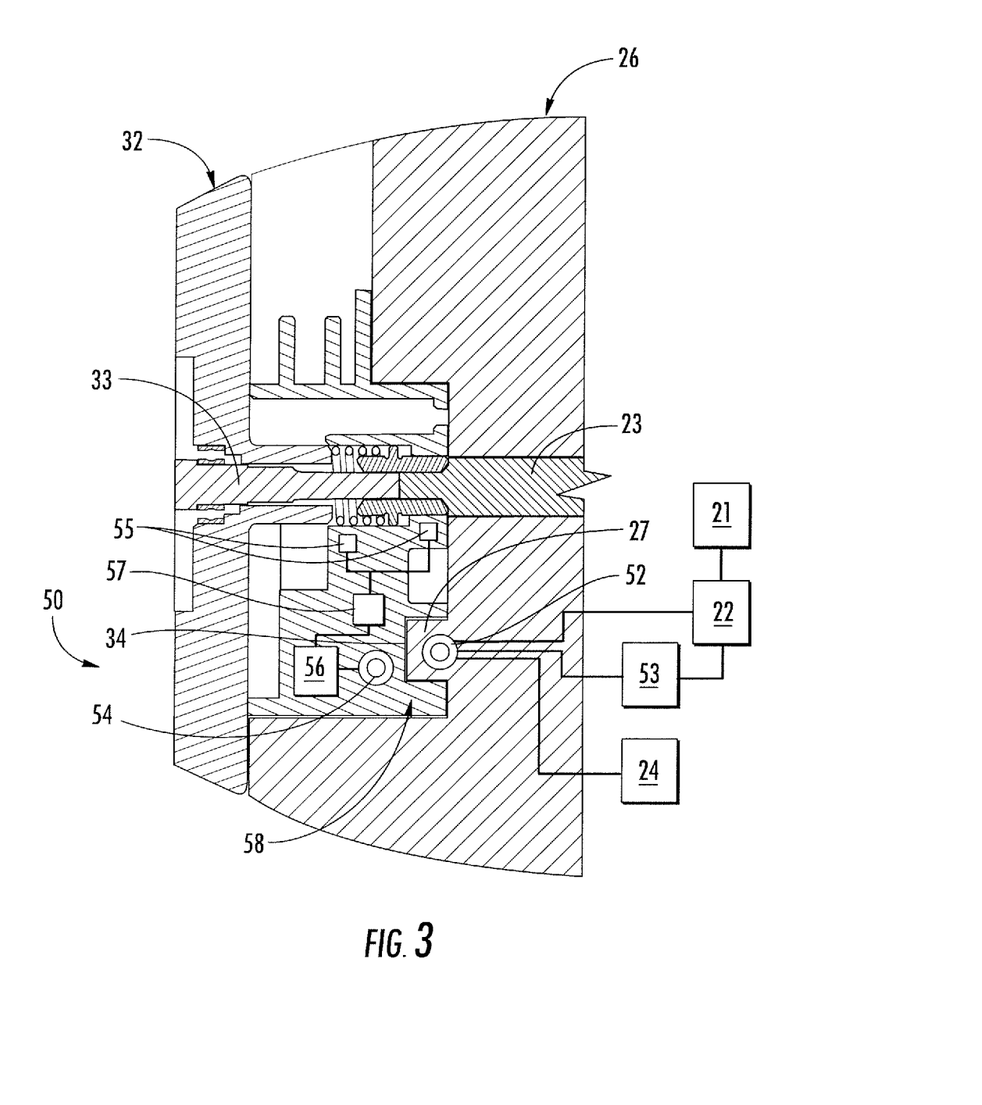
FIG. 3 is a cross-sectional view taken along the section line 3-3 of FIG. 1 illustrating an electrical interface between the handle and the adaptor of the instrument of FIG. 1.
Figure 4:
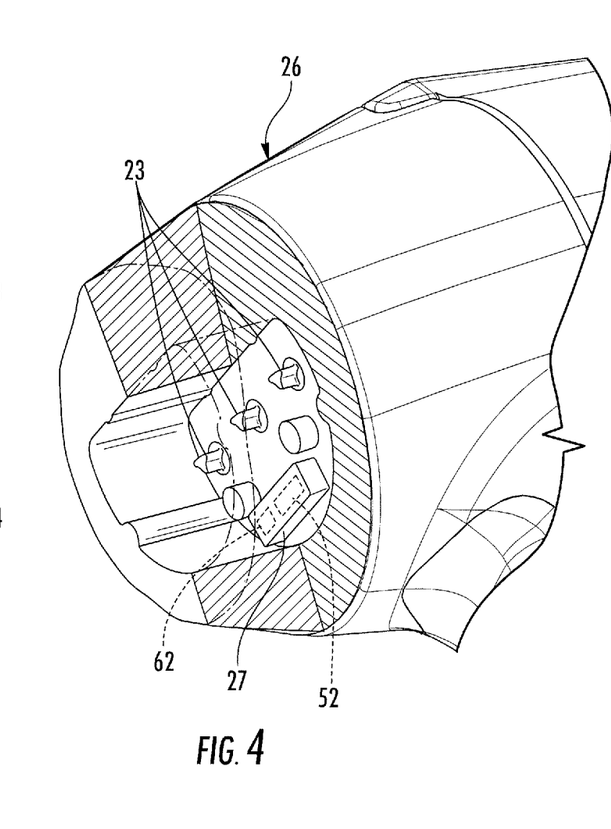
FIG. 4 is a cut-away perspective view of the adaptor receiver of the handle of FIG. 2.
Figure 5:
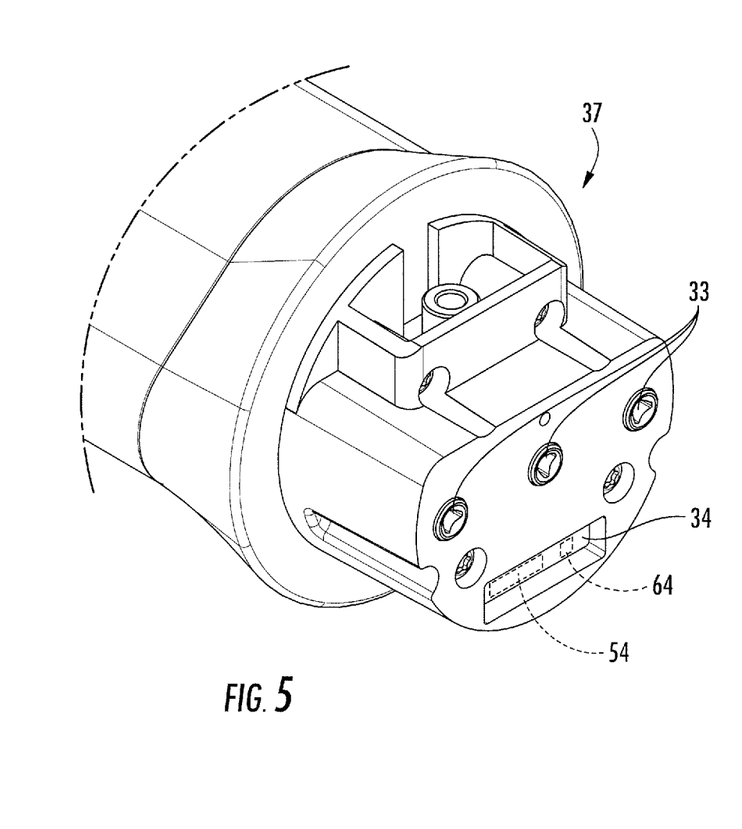
FIG. 5 is an enlarged view of the area of detail of FIG. 2 illustrating the handle connector of the adaptor of FIG. 2.

Referring now to FIGS. 1-3, a surgical instrument 10 is provided in accordance with the present disclosure including a handle 20, an adaptor 30, and a disposable loading unit 40. The adaptor 30 includes a handle connector 32 at a proximal end thereof and the handle 20 defines an adaptor receiver 26 for receiving the handle connector 32 to releasably couple the adaptor 30 to the handle 20. The disposable loading unit 40 includes a loading unit connector 42 at a proximal end thereof and the adaptor 30 defines a loading unit receiver 36 adjacent a distal end thereof to releasably couple the disposable loading unit 40 to the adaptor 30. The disposable loading unit 40 includes an end effector assembly 140 including first and second jaw members 142, 144 that are moveable relative to one another and are configured to act on tissue.

An exemplary embodiment of a surgical instrument is disclosed in commonly owned and co-pending U.S. patent application Ser. No. 13/484,975 filed May 31, 2012, and now published as U.S. Patent Publication No. 2012/0253329 on Oct. 4, 2012 the contents of which are hereby incorporated by reference in its entirety.

With particular reference to FIG. 3, an electrical interface 50 is disposed within the adaptor receiver 26 and the handle connector 32. The electrical interface 50 is a non-contact electrical interface that transmits energy from the handle 20 to the adaptor 30 and transmits data signals from the adaptor 30 and/or the disposable loading unit 40 to the handle 20, between the adaptor receiver 26 and the handle connector 32, as detailed below. It is contemplated that control signals are transmitted by the electrical interface 50 from the handle 20 to the adaptor 30. The handle 20 may include a display 25 (FIG. 2) configured to display information from the data signals from the adaptor 30 and/or the disposable loading unit 40 to a user of the surgical instrument 10.

Referring now to FIGS. 2-5, the handle 20 is operatively associated with an energy source 24 that provides energy to the handle 20 and the adaptor 30. It is within the scope of this disclosure that the handle 20 includes a first energy source for the handle 20 and a second energy source for the adaptor 30. The energy source 24 may be disposed within the handle 20 or disposed external to the handle 20. The energy source 24 may be a battery, a wall outlet, or an electrosurgical generator. The energy source 24 is electrically connected to a proximal coil 52 of the electrical interface 50 to provide the proximal coil 52 with a substantially constant supply of energy. The energy source 24 may be directly wired to the proximal coil 52.

The adaptor receiver 26 of the handle 20 includes a protrusion 27 extending distally therefrom. The proximal coil 52 of the electrical interface 50 is disposed within the protrusion 27 of the handle 20. The adaptor receiver 26 may include one or more drive shafts 23 configure to mechanically manipulate (e.g., rotate or translate) internal components of the adaptor 30.

The handle connector 32 of the adaptor 30 includes one or more input shafts 33 extending therefrom, and defines a recess 34 formed therein. The input shafts 33 are configured to non-rotatably interface with the one or more drive shafts 23 of the handle 20. The handle connector 32 of the adaptor 30 includes a distal coil 54 of the electrical interface 50 that is positioned adjacent the recess 34. The recess 34 of the adaptor 30 is sized and configured to receive the protrusion 27 of the handle 20.

The distal coil 54 or the electrical interface 50 is electrically connected to an energy storage device 56 of the adapter 30 to provide energy, typically as a constant current, to the energy storage device 56 as detailed below. The energy storage device 56 of the handle 20 is configured to energize a plurality of sensors 55 of the adaptor 30. The energy storage device 56 may be a capacitor, a capacitive circuit, or a battery.

The plurality of sensors 55 are disposed about the adaptor 30 to detect various conditions of the adaptor 30 or of the environment (e.g., if loading unit is connected, if the adaptor 30 is connected to a handle, if the drive shafts 23 are rotating, the torque of the drive shafts 23, the temperature within the adaptor 30, etc.). The plurality of sensors 55 provides input to a data signal processor 57 in the form of data signals. The data signals may be digital or analog signals. The data signal processor 57 may be a voltage to current converter that converts data signals of the plurality of sensors to high frequency signals for transmission across the electrical interface 50, as detailed below. The data signal processor 57 transmits the data signals to the distal coil 54 of the adaptor 30. It is contemplated that the data signal processor 57 may be directly wired to the distal coil 54.

Figure 6:
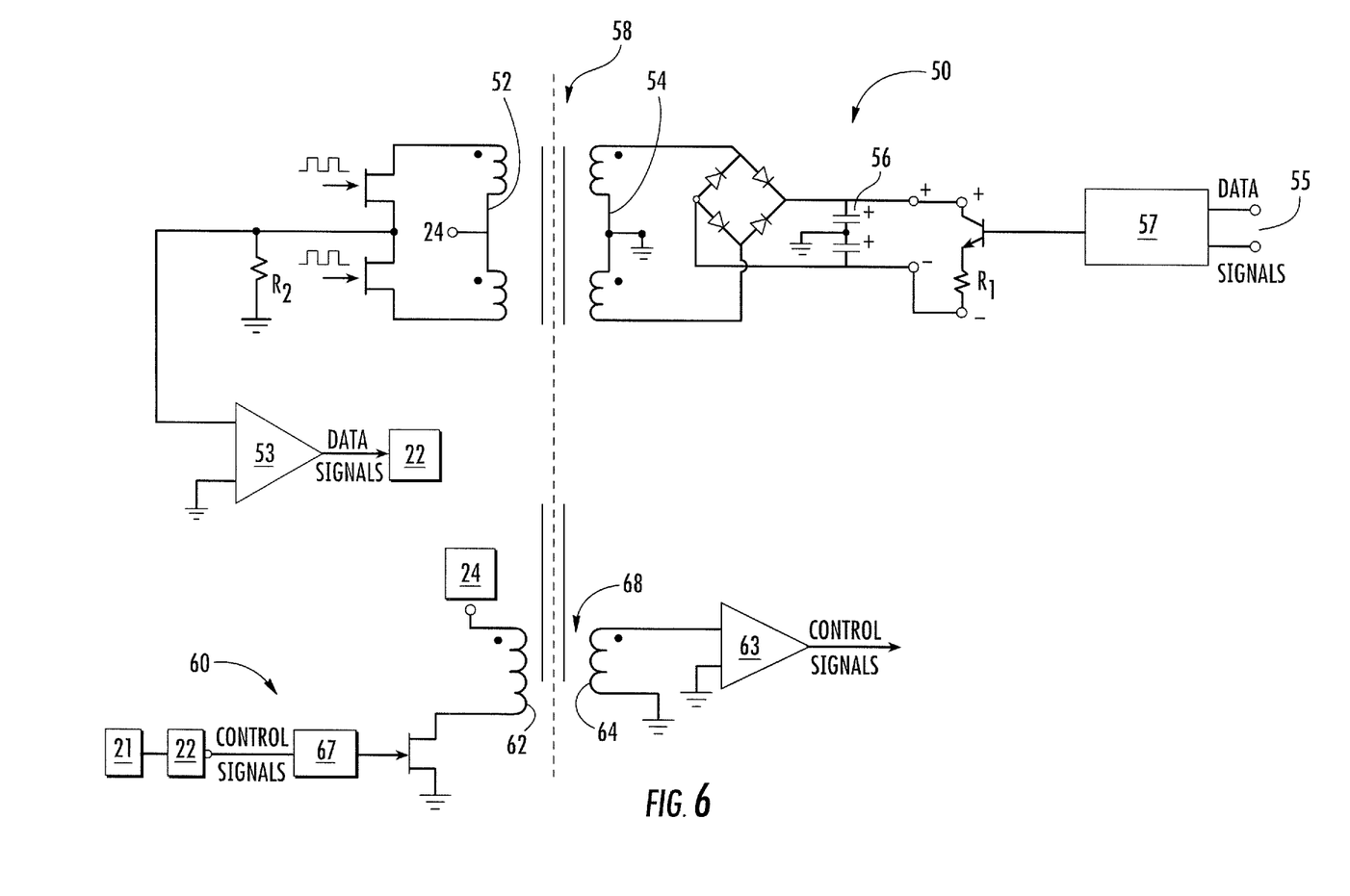
FIG. 6 is a schematic view of the electrical interface between the handle and the adaptor of FIG. 3.

With reference to FIGS. 3 and 6, when the handle connector 32 of the adaptor 30 is received within the adaptor receiver 26 of the handle 20, the recess 34 receives the protrusion 27. When the recess 34 of the adaptor 20 is received within the protrusion 27 of the handle 20, the proximal and distal coils 52, 54 form a data transformer 58 to wirelessly transfer energy (e.g., inductively transfer) from the proximal coil 52 to the distal coil 54 and to wirelessly transfer (e.g., inductively transfer) the data signals from the distal coil 54 to the proximal coil 52. It will be appreciated that, when the adaptor 30 is coupled to the handle 20, a gap is defined between the proximal and distal coils 52, 54.

The energy source 24 of the handle 20 provides energy to the proximal coil 52. The energy provided by the energy source 24 may be constant or fluctuate at a low frequency (i.e., fluctuate below 100 Hz). It will be appreciated that the high frequency signals fluctuate at a high frequency (i.e., over 20 KHz) relative to the frequency of any fluctuation in the energy provided by the energy source 24 to avoid interference between the provided energy and the high frequency signals. The energy received by the proximal coil 52 is inductively transferred across the gap and across the data transformer 58 to the distal coil 54. The transferred energy may be stored in the energy storage device 56 and/or used to energize components of the adaptor 30 including but not limited to the data signal processor 57 and the plurality of sensors 55.

The data signals from the plurality of sensors 55 of the adaptor 30 are generated as a voltage that is passed through the data signal processor 57 of the adaptor 30 before being sent to the distal coil 54. The data signal processor 57 converts the data signals from the plurality of sensors to a high frequency signal using voltage to current conversion. The secondary current circuit affords the opportunity to measure the primary current modulated by R1 to receive signals from the secondary circuit. The high frequency current signals are inductively transferred across the gap and across the data transformer 58 (i.e., from the distal coil 54 to the proximal coil 52). The high frequency signals from the proximal coil 52 may pass through a filter 53 that reconstructs the data signals of the plurality of sensors 55 from the high frequency signals. The filter 53 may be a high-pass filter that detects the high frequency signals and reconstructs the data signals from the detected high frequency signals. The filter 53 may have a low corner frequency to filter the high frequency signals from fluctuations in the energy provided by the energy source 24.

The reconstructed data signals are then transmitted to a processor 22 disposed within the handle 20, as shown in FIG. 2. The processor 22 may be electrically coupled or wirelessly coupled to the display 25 of the handle 20 and configured to transmit information from the data signals of the sensors 55 to the display 25. It is contemplated that the processor 22 and/or the display are remote to the surgical instrument 10. When the processor 22 is remote to the surgical instrument 10, the reconstructed data signal may be transmitted wirelessly from the handle 20 to the processor 22.

The handle 20 may include a control interface 21 for activating various components of the adaptor 30 or loading unit 40. The control interface 21 is in electrical communication with the processor 22 to provide input from a user to the processor 22. The processor 22 may wirelessly transmit (e.g., inductively transfer) control signals to the adaptor 30 or loading unit 40 based on the input from the control interface 21 and/or the reconstructed data signals (e.g., real-time feedback from the operation of the surgical instrument 10). The control signals may be digital or analog signals.

The electrical interface 50 may include a control circuit 60 for transmitting the control signals. The control circuit 60 includes a proximal control coil 62 and a distal control coil 64 which form a control transformer 68 when the handle connector 32 of the adaptor 30 is received within the adaptor receiver 26 of the handle 20. The proximal control coil 62 is disposed within the protrusion 27 of the handle 20 adjacent to but electrically shielded from the proximal coil 52. The distal control coil 64 is positioned adjacent to the recess 34 of the adaptor 30 and to the distal coil 54 but is electrically shielded from the distal coil 54. It will be appreciated that the control transformer 68 is electrically shielded or isolated from the data transformer 58 such that the data signals do not interfere with the control signals.

The control signals from the processor 22 of the handle 20 are transmitted to a control signal processor 67 thereof. The control signal processor 67 is substantially similar to the data signal processor 57 and converts the control signals from the processor 22 to high frequency control signals for transmission across the control transformer 68. The high frequency control signals are transmitted from the control signal processor 67 to the proximal control coil 62. The proximal control coil 62 receives energy from the energy source 24 of the handle 20. It is also contemplated that the proximal control coil 62 receives energy from a separate and distinct energy source (not shown). The energy received by the proximal control coil 62 is inductively transferred across the control transformer 68 to the distal control coil 64.

The high frequency control signals are inductively transmitted across the control transformer 68 from the proximal control coil 62 to the distal control coil 64. The distal control coil 64 transmits the high frequency control signals to the control filter 63 that detects the high frequency control signals within the energy transmitted across the control transformer 68 and reconstructs the control signals therefrom. The reconstructed control signals are then transmitted to various components of the adaptor 30 and/or the loading unit 40.

Figure 7:
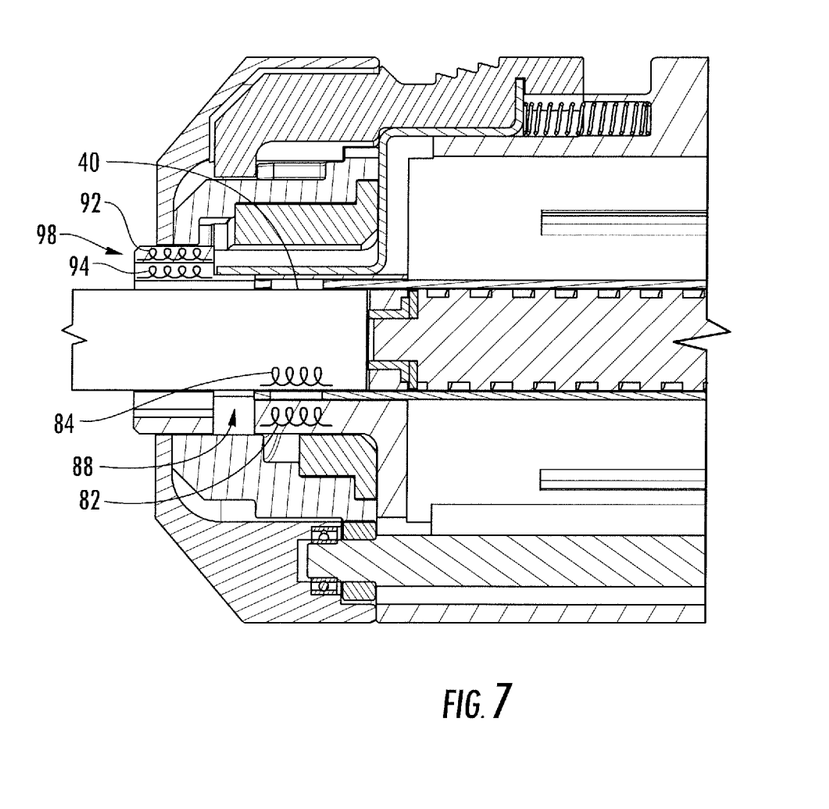
FIG. 7 is a cross-sectional view taken along section line 7-7 of FIG. 1 illustrating an electrical interface between the adaptor and the loading unit of FIG. 1.

Referring to FIG. 7, the surgical instrument 10 may include an electrical interface 80 formed between the loading unit receiver 36 of the adaptor 30 and the loading unit connector 42 of the loading unit 40. The electrical interface 80 is substantially similar to the electrical interface 50, as such, for reasons of brevity, electrical interface 80 will not be detailed herein. The electrical interface 80 is a non-contact interface that inductively transfers energy from the adaptor 30 to the loading unit 40 and inductively transfers data signals from the loading unit 40 to the adaptor 30. It is also contemplated that the electrical interface 80 includes a control circuit 90 that inductively transfers control signals from the adaptor 30 to the loading unit 40 substantially similar to the control circuit 60 detailed above, as such for reasons of brevity control circuit 90 will not be detailed herein. The electrical interface 80 may transmit and receive signals (e.g., data signals and control signals) from the electrical interface 50 and/or the processor 22.

With additional reference to FIG. 2, the loading unit 40 may also include a plurality of sensors 85 disposed thereabout. The plurality of sensors 85 of the loading unit 40 are substantially similar to the plurality of sensors 55 of the adaptor 30 and are configured to detect various conditions of the loading unit 40 or of the environment (e.g., if the end effector 140 (FIG. 2) is open, thickness of tissue within the end effector 140, the temperature within the loading unit 40, etc.). The plurality of sensors 85 provides input to the electrical interface 80 in the form of data signals.

It is also contemplated that a surgical instrument (not shown) includes only a handle substantially similar to handle 20 and a disposable loading unit substantially similar to disposable loading unit 40 connectable to the handle 20 (i.e., no adaptor 30 is used). The surgical instrument may include an electrical interface substantially similar to the electrical interface 50 disposed within the handle and the disposable loading unit to transmit energy from the handle to the disposable loading unit and to transmit data signals from the disposable loading unit to the handle.

The wireless transmission detailed herein may be radio frequency, optical, WIFI, Bluetooth® (an open wireless protocol for exchanging data over short distances (using short length radio waves) from fixed and mobile devices, ZigBee® (a specification for a suite of high level communication protocols using small, low-power digital radios based on the IEEE 802.15.4-2003 standard for wireless personal area networks (WPANs)), etc.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto.

What is claimed is:

1. A surgical instrument comprising:
   a handle including:
      a protrusion; and
      a proximal electrical coil disposed within the protrusion;
   an adaptor including:
      a proximal end releasably coupled to a distal end of the handle;
      a recess configured to receive the protrusion; and
      a distal electrical coil disposed at a location adjacent the recess; and
   a non-contact electrical interface configured to wirelessly transfer energy through the proximal and distal electrical coils from the handle to the adaptor and configured to wirelessly transmit data from the adaptor to the handle.

2. The surgical instrument of claim 1, wherein when the adaptor is coupled to the handle the proximal and distal electrical coils form a transformer.

3. The surgical instrument of claim 1, wherein the proximal electrical coil inductively transfers energy to the distal electrical coil, and the distal electrical coil inductively transmits data to the proximal electrical coil.

4. The surgical instrument of claim 1, wherein the proximal electrical coil inductively transfers a constant supply of energy to the distal electrical coil.

5. The surgical instrument of claim 4, wherein the handle includes an energy source disposed therein, wherein the energy source is electrically coupled to the proximal electrical coil.

6. The surgical instrument of claim 5, wherein the adaptor includes an energy storage device disposed therein, wherein the energy storage device is electrically coupled to the distal electrical coil, and wherein the energy storage device is configured to store energy from the energy source.

7. The surgical instrument of claim 6, wherein the electrical interface includes a signal processor disposed within the adaptor, and wherein the energy storage device is configured to energize the signal processor.

8. The surgical instrument of claim 6, wherein the electrical interface includes a signal processor disposed within the adaptor, the signal processor configured to create high frequency signals from data signals and transmit the high frequency signals to the distal electrical coil.

9. The surgical instrument of claim 8, wherein the electrical interface further includes a plurality of sensors disposed within the adaptor, the plurality of sensors configured to generate and transmit data signals to the signal processor.

10. The surgical instrument of claim 9, wherein the energy storage device is configured to energize the plurality of sensors.

11. The surgical instrument of claim 8, wherein the electrical interface includes a filter disposed within the handle, wherein the filter is electrically coupled to the proximal electrical coil, and wherein the filter is configured to reconstruct the data signals from the high frequency signals.

12. The surgical instrument of claim 11, wherein the handle includes a display configured to display information from the reconstructed data signals to a user.

13. The surgical instrument of claim 1, wherein the electrical interface includes a control circuit configured to wirelessly transmit control signals from the handle to the adaptor.

14. The surgical instrument of claim 13, wherein the control circuit includes a proximal control coil disposed within the protrusion and a distal control coil disposed within the adaptor at a location adjacent to the recess, the proximal and distal control coils forming a control transformer when the adaptor is coupled to the handle to inductively transmit control signals from the handle to the adaptor.

15. The surgical instrument of claim 14, wherein the handle includes a control interface and the electrical interface includes a processor disposed within the handle, the processor configured to receive control inputs from the control interface and to receive data from the adaptor, the processor configured to generate control signals from the control inputs and from the data, the processor configured to transmit the control signals to the proximal control coil.

16. A surgical instrument comprising:
   a handle;
   an adaptor including a proximal end releasably coupled to a distal end of the handle;
   a loading unit releasably coupled to a distal end of the adaptor;
   a first non-contact electrical interface configured to wirelessly transfer energy from the handle to the adaptor and configured to wirelessly transmit data from the adaptor to the handle; and
   a second non-contact electrical interface configured to inductively transfer energy from the adaptor to the loading unit and configured to inductively transmit data signals from the loading unit to the adaptor.

* * * * *